US009662505B2

(12) United States Patent
Kibler et al.

(10) Patent No.: US 9,662,505 B2
(45) Date of Patent: May 30, 2017

(54) IMPLANTABLE MEDICAL DEVICE, MEDICAL SYSTEM AND METHOD FOR DATA COMMUNICATION

(71) Applicant: BIOTRONIK SE & CO. KG, Berlin (DE)

(72) Inventors: Andrew B. Kibler, Lake Oswego, OR (US); J. Christopher Moulder, Portland, OR (US); R. Hollis Whittington, Portland, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 15/173,454

(22) Filed: Jun. 3, 2016

(65) Prior Publication Data
US 2016/0279431 A1 Sep. 29, 2016

Related U.S. Application Data

(62) Division of application No. 14/157,389, filed on Jan. 16, 2014, now Pat. No. 9,381,365.
(Continued)

(51) Int. Cl.
*A61N 1/00* (2006.01)
*A61N 1/372* (2006.01)
(Continued)

(52) U.S. Cl.
CPC ....... *A61N 1/37276* (2013.01); *A61N 1/3708* (2013.01); *A61N 1/378* (2013.01); *A61N 1/3727* (2013.01); *A61N 1/37217* (2013.01)

(58) Field of Classification Search
CPC .. A61N 1/37276; A61N 1/3708; A61N 1/378; A61N 1/375; A61N 1/37211
See application file for complete search history.

(56) References Cited

U.S. PATENT DOCUMENTS 6,076,016 A 6/2000 Feierbach
6,456,887 B1 9/2002 Dudding et al.
(Continued)

FOREIGN PATENT DOCUMENTS

WO 2008/016194 2/2008

OTHER PUBLICATIONS

Wegmueller, Marc Simon, "Intra-Body Communication for Biomedical Sensor Networks", 2007, Diss. ETH No. 17323, Switzerland, 173 pages.
(Continued)

*Primary Examiner* — Mallika D Fairchild
(74) *Attorney, Agent, or Firm* — Arc IP Law, PC; Joseph J. Mayo

(57) ABSTRACT

An implantable medical device including a data communication device that includes a device to alter and/or generate an oscillatory electric field imposed on body tissue surrounding the implantable medical device when the implantable medical device is in its implanted state. The device that alters an oscillatory electric field modulates an impedance of body tissue surrounding the implantable medical device when the implantable medical device is in its implanted state and within an oscillatory electric field. The device that alters an oscillatory electric field includes a device that generates an oscillatory electric field that is phase-synchronized with an oscillatory electric field imposed on body tissue surrounding the implantable medical device when the implantable medical device is in its implanted state.

10 Claims, 5 Drawing Sheets

Related U.S. Application Data

(60) Provisional application No. 61/761,707, filed on Feb. 7, 2013.

(51) Int. Cl.
*A61N 1/37* (2006.01)
*A61N 1/378* (2006.01)

(56) References Cited

U.S. PATENT DOCUMENTS

| | | |
|---|---|---|
| 7,945,333 B2 | 5/2011 | Jacobson |
| 8,547,248 B2 | 10/2013 | Zdeblick et al. |
| 8,612,013 B2 | 12/2013 | Forsell |
| 2004/0167587 A1 | 8/2004 | Thompson |
| 2007/0293908 A1 | 12/2007 | Cowan et al. |
| 2008/0294062 A1 | 11/2008 | Rapoport et al. |
| 2009/0204170 A1 | 8/2009 | Hastings et al. |
| 2009/0228071 A1 | 9/2009 | Bourget |
| 2010/0125315 A1 | 5/2010 | Parramon et al. |
| 2011/0125214 A1 | 5/2011 | Goetz et al. |
| 2011/0288615 A1 | 11/2011 | Armstrong et al. |
| 2012/0004708 A1 | 1/2012 | Chen et al. |
| 2012/0029323 A1 | 2/2012 | Zhao |
| 2012/0101545 A1 | 4/2012 | Wahlstrand et al. |

OTHER PUBLICATIONS

European Search Report issued for EP Application No. 14152632.7 dated Apr. 25, 2014, 8 pages.

IMPLANTABLE MEDICAL DEVICE, MEDICAL SYSTEM AND METHOD FOR DATA COMMUNICATION

This application is a divisional application of U.S. patent application Ser. No. 14/157,389, filed on 16 Jan. 2014, which claims the benefit of U.S. Provisional Patent Application 61/761,707, filed on 7 Feb. 2013, the specifications of which are hereby incorporated herein by reference.

BACKGROUND OF THE INVENTION

Field of the Invention

At least one embodiment of the invention generally relates to implantable medical devices and data communication from implantable medical devices to an external device.

Description of the Related Art

Typically, implantable devices, in particular implantable medical devices, such as implantable therapy and/or monitoring devices including pacemakers, cardioverters and defibrillators or the like, may include data communication means to transmit data from the implantable medical device to an external device or vice versa.

A system for data communication with a medical device thus, generally, includes an implantable medical device and an external device such as a programmer.

A typical implantable medical device comprises a battery, a monitoring and/or therapy control unit, in some cases additionally one or more therapy units such as stimulation units and a memory for storing control program and/or data sensed by the implantable medical device. If the implantable medical device is a pacemaker or an implantable cardioverter/defibrillator (ICD), generally, the therapy units comprise stimulation units for generating and delivering electric stimulation pulses to a patient's heart tissue (myocardium).

Generally, in order to transmit data sensed by the implantable medical device to an external device, a telemetry unit may be provided. Typically the telemetry unit may be configured to allow bidirectional data communication, that is, the telemetry unit may transmit and receive data wirelessly.

Limited battery capacity of an implantable medical device generally calls for energy-efficient data communication. An implantable medical device with limited battery power typically requires a low power communication scheme in order to program it and to download acquired data. With extremely low power communication, generally, more data may be transmitted more often.

Typical communication schemes used for data communication by a telemetry unit involve either RF or magnetic communication. Generally, RF frequencies of ~400 or ~900 MHz or magnetic coupling in the 100s of kHz range require several mA of current to transmit and receive data. Such high current requirements are typically out of reach of devices with battery capacities of at most a few hundred mAh.

In addition, RF schemes generally require large antennas and magnetic coupling generally requires large transmit and receive coils for communication. The space available in miniaturized implants, typically, would not allow such large coils or antennas.

In view of the above, there is a need for a low power communication scheme that does not employ RF or magnetic coupling.

BRIEF SUMMARY OF THE INVENTION

Objectives of the invention according to at least one embodiment of the invention include providing an alternative implantable device and an alternative data communication method that result in little battery drain from the medical device's battery.

According to one or more embodiments of the invention, an implantable medical device may be provided that includes one or more data communication devices which may include one or more devices that may alter an oscillatory electric field imposed on body tissue surrounding the implantable medical device when the implantable medical device is in its implanted state. In embodiments of the invention, the one or more data communications devices may include one or more devices that may generate a second oscillatory electric field, which may be synchronized to a first oscillatory electric field imposed on body tissue surrounding the implantable medical device.

In at least one embodiment, the one or more devices that may alter an oscillatory electric field may modulate an impedance of a volume of body tissue surrounding the implantable medical device when the implantable medical device is in its implanted state and within an oscillatory electric field.

In embodiments of the invention, the one or more devices that may alter an oscillatory electric field may include one or more devices that may generate an oscillatory electric field that is phase-synchronized with an oscillatory electric field imposed on body tissue surrounding the implantable medical device when the implantable medical device is in its implanted state.

In at least one embodiment, the one or more devices that may generate a second oscillatory electric field may include one or more devices that may sense the phase of a first oscillatory electric field by the implantable medical device, and one or more devices that may generate the second oscillatory electric field in a manner that is phase synchronized to the sensed first electric field while the medical device is in its implanted state.

One or more embodiments of the invention may use modulation of impedance within an electric field to communicate between a small medical device implanted in the heart or body and an external programmer/communication device, which may also be implanted in the body. Alternatively, embodiments of the invention may generate a small electric field to facilitate this same communication, thus modulating the electric field imparted on the implantable medical device. In one or more embodiments, the external device may usecutaneous or implanted electrodes to impart an oscillatory electric field on the body that encompasses the medical device.

By way of one or more embodiments, during impedance modulation, the medical device, within the field, may alternate shorting and opening of an internal connection between two electrodes on its surface to change the impedance across the space of the device. In at least one embodiment, the changes in impedance may be sensed by the external device as changes in either current or voltage. The changes in voltage or current may be modulated to form a communication scheme to transmit data. In one or more embodiments, the external device's electric field may be additionally used to transmit data to the implanted medical device.

According to at least one embodiment of the invention, during electric field transmission, the external device may use cutaneous or implanted electrodes to impart an oscillatory electric field on the body that encompasses the implanted medical device. The implanted device, in one or more embodiments, may then monitor this field and may generate a small electric field that may be phase-synchronized with the external device's field in order to facilitate reception of this small field by the external device using a lock-in (phase-locked) amplifier. The external device's electric field may not be continuously generated, and may be additionally used to transmit data to the implanted medical device. In one or more embodiments, the small changes in the body's electric field may be sensed by the external device as changes in voltage or current and may be demodulated to form a communications scheme from the implanted device to the external device.

Embodiments of the invention may allow an implantable medical device with limited battery supply the ability to transmit increased amount of data while using very little power. Data transmission, in at least one embodiment, may be achieved by modulating an electric field imparted on the body by altering the impedance of the transmission medium and read by the receiver as changing voltage or current. In embodiments of the invention, continuous medium rate data transmission may be achieved while using very little battery power.

Preferably, in at least one embodiment, the implantable medical device during impedance modulation may further include at least one switching device and at least two electrodes that may be connected to the at least one switching device, such that the at least two electrodes may be electrically connected or disconnected, respectively, by the at least one switching device. In at least one embodiment, the at least two electrodes may cause a change of impedance when the implantable medical device is in its implanted state and the electrodes may be connected or disconnected, respectively, using the at least one switching device.

The at least one switching device, in at least one embodiment, may be connected to a switch control that may sense an oscillatory electric field imposed on body tissue surrounding the implantable medical device when the implantable medical device is in its implanted state. Thus, in one or more embodiments, it is possible to synchronize connecting and disconnecting of the at least two implantable electrodes with the oscillatory electric field imposed on the body tissue surrounding or encompassing the implantable medical device.

To implement such synchronizing, in at least one embodiment of the invention, the switch control may include a phase-locked loop (PLL) and a frequency divider, wherein the phase-locked loop may lock in a frequency of an oscillatory electric field imposed on body tissue surrounding the implantable medical device when the implantable medical device is in its implanted state. The frequency divider, in embodiments of the invention, may be connected to the phase-locked loop and may divide a frequency signal outputted by the phase-locked loop. Thus, in at least one embodiment, the implantable medical device may generate a code that may represent data to be transmitted from the implantable medical device to an external device, wherein the clock for such code may be a fraction of the frequency of the oscillatory electric field imposed on the body tissue surrounding the implantable medical device. According to one or more embodiments, if the frequency of the divided signal is sufficiently low, on the order of 1:100, the need for the PLL would be eliminated. In this case the maximum decrease in efficiency due to lack of phase lock with the external electric field may be one percent, or one out of 100 cycles of the imparted field.

According to at least one embodiment, the switch control may be connected to the at least two electrodes and may sense an oscillatory electric field imposed on body tissue via the at least two electrodes. The switch control, in embodiments of the invention, may include a band-pass filter, wherein the band-pass filter may filter a signal fed to the phase-locked loop.

In at least one embodiment, the at least one device that may alter an oscillatory electric field may include at least one field generating device that may generate an oscillatory electric field that may be phase-synchronized with an oscillatory electric field imposed on body tissue surrounding the implantable medical device when the implantable medical device is in its implanted state. An implantable medical device according to at least one embodiment may further include at least one field generation control device that may be operatively connected to the at least one field generating device and may control the at least one field generating device in response to an oscillatory electric field imposed on body tissue surrounding the implantable medical device when the implantable medical device is in its implanted state.

Objectives of the invention may be further achieved by a data communication system including an implantable medical device as described above and an external device that may include or may be connected to at least two cutaneous or implanted electrodes. In at least one embodiment, the external device may include at least one external field generating device that may generate an oscillatory electric field that may be imposed across the implanted medical device via the at least two cutaneous or implanted electrodes. The external device, in one or more embodiments, may include at least one sensing device that may sense alterations of body impedance and/or an oscillatory electric field generated by the implantable medical device when the implantable medical device is in its implanted state.

The external device, in one or more embodiments, may include a lock-in amplifier, an AM demodulator that may demodulate the amplitude-modulated signals and an analog-to-digital converter, wherein the analog-to-digital converter may be operatively connected to the AM demodulator and the lock-in amplifier, and wherein the analog-to-digital converter may produce a signal that may represent a signal transmitted by the implantable medical device.

Objectives of the invention according to at least one embodiment may be further achieved by a method of communicating data from an implantable medical device to an external device, wherein the method may include:
 imposing an oscillatory electric field in body tissue encompassing an implantable medical device,
 sensing the imposed oscillatory electric field using the implantable medical device,
 altering the oscillatory electric field using the implantable medical device by inducing an alternating change of impedance using the implantable medical device or by generating a small oscillatory electric field using the implantable medical device,—and/or
 generating an oscillatory electric field that may be phase synchronized to the imposed electric field using the implantable device, and sensing the change of impedance or the small oscillatory electric field generated by the implantable medical device, respectively, using an external device having or being connected to at least two cutaneous electrodes.

Preferably, in at least one embodiment, the step of altering the oscillatory electric field using the implantable medical device may be performed using at least two electrodes that may be operatively connected to or be part of the implantable medical device, and at least one switch that may be operatively connected to the at least two electrodes. In embodiments of the invention, the at least one switching device may connect and disconnect the at least two electrodes in an alternating manner according to a code-representing data that may be transmitted from the implantable medical device to the external device. In one or more embodiments, the alternating connecting and disconnecting may cause a detectable change of impedance for the imposed oscillatory electric field.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
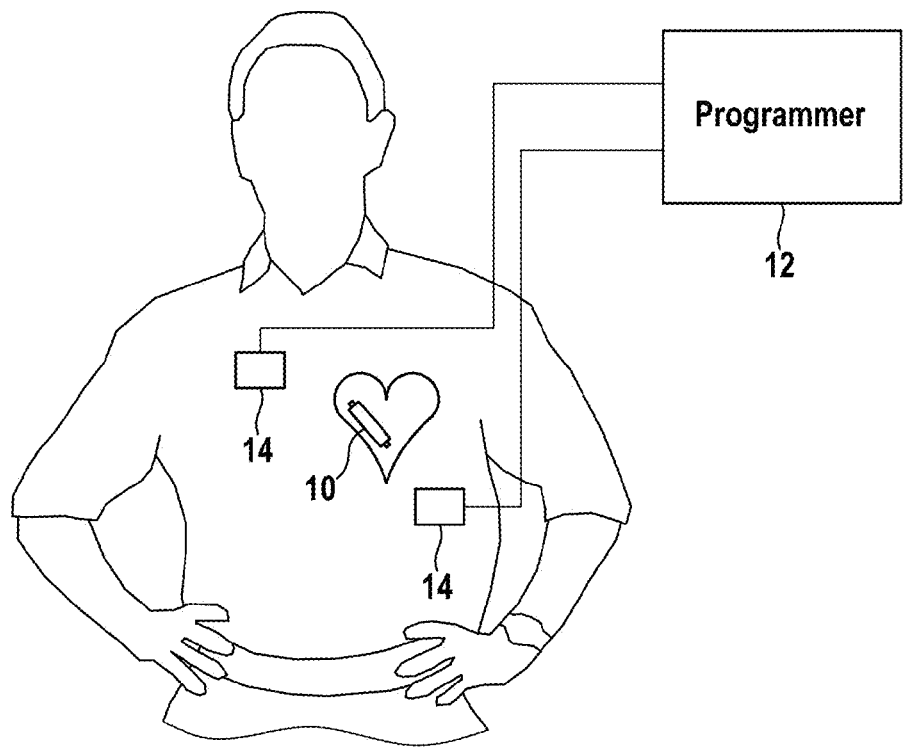
FIG. 1 shows a representation of a communication system, including an implantable medical device in its implanted state and an external device, according to one or more embodiments of the invention.

FIG. 1 shows a representation of a communication system, comprising including an implantable medical device in its implanted state and an external device, according to one or more embodiments of the invention. As shown, one or more embodiments of the invention, may utilize an implanted pacemaker such as an implantable medical device 10, a programmer/communication device such as external device 12, and cutaneous electrodes 14 that may be placed on either side of the heart. In at least one embodiment, the external device 12 may induce an oscillating electric field between the electrodes at 100 kHz-1 MHz, for example, at a known voltage or current. The medical device implanted in the heart may be between the two electrodes in embodiments of the invention.

Figure 2:
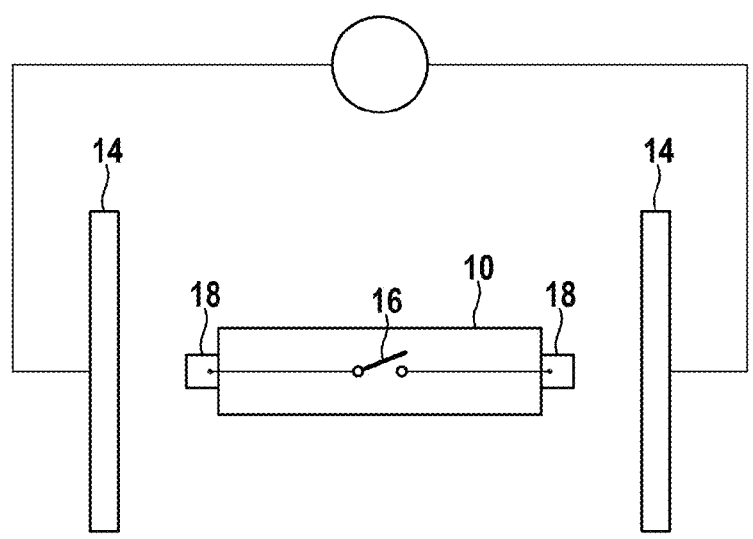
FIG. 2 shows a more abstract representation of the system depicted in FIG. 1 according to one or more embodiments of the invention.

FIG. 2 shows a more abstract representation of the system depicted in FIG. 1 according to one or more embodiments of the invention.

Figure 3:
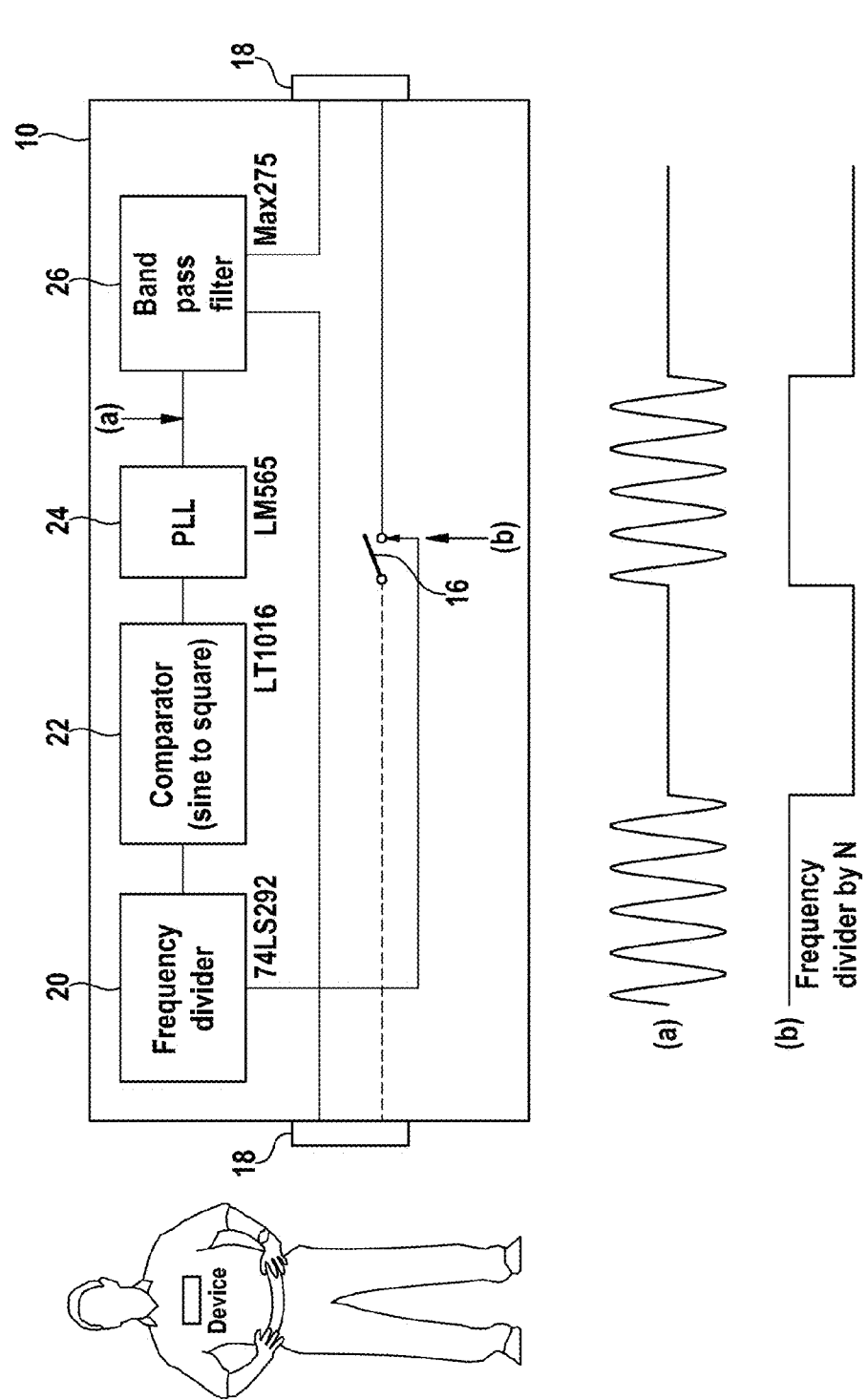
FIG. 3 shows a more detailed representation of an implantable device according to one or more embodiments of the invention.

FIG. 3 shows a more detailed representation of an implantable device 10 according to one or more embodiments of the invention. It should be noted that an implantable medical device, according to embodiments of the invention, such as an implantable heart stimulator may include a battery, a monitoring and/or therapy control unit, one or more therapy units such as stimulation units and a memory that may store control program and/or data sensed by the implantable medical device. If the implantable medical device is a pacemaker or an implantable cardioverter/defibrillator (ICD), in at least one embodiment, the therapy units may include stimulation units that may generate and deliver electric stimulation pulses to a patient's heart tissue (myocardium). Stimulation units may be connected to stimulation electrode leads in embodiments of the invention.

Figure 4:
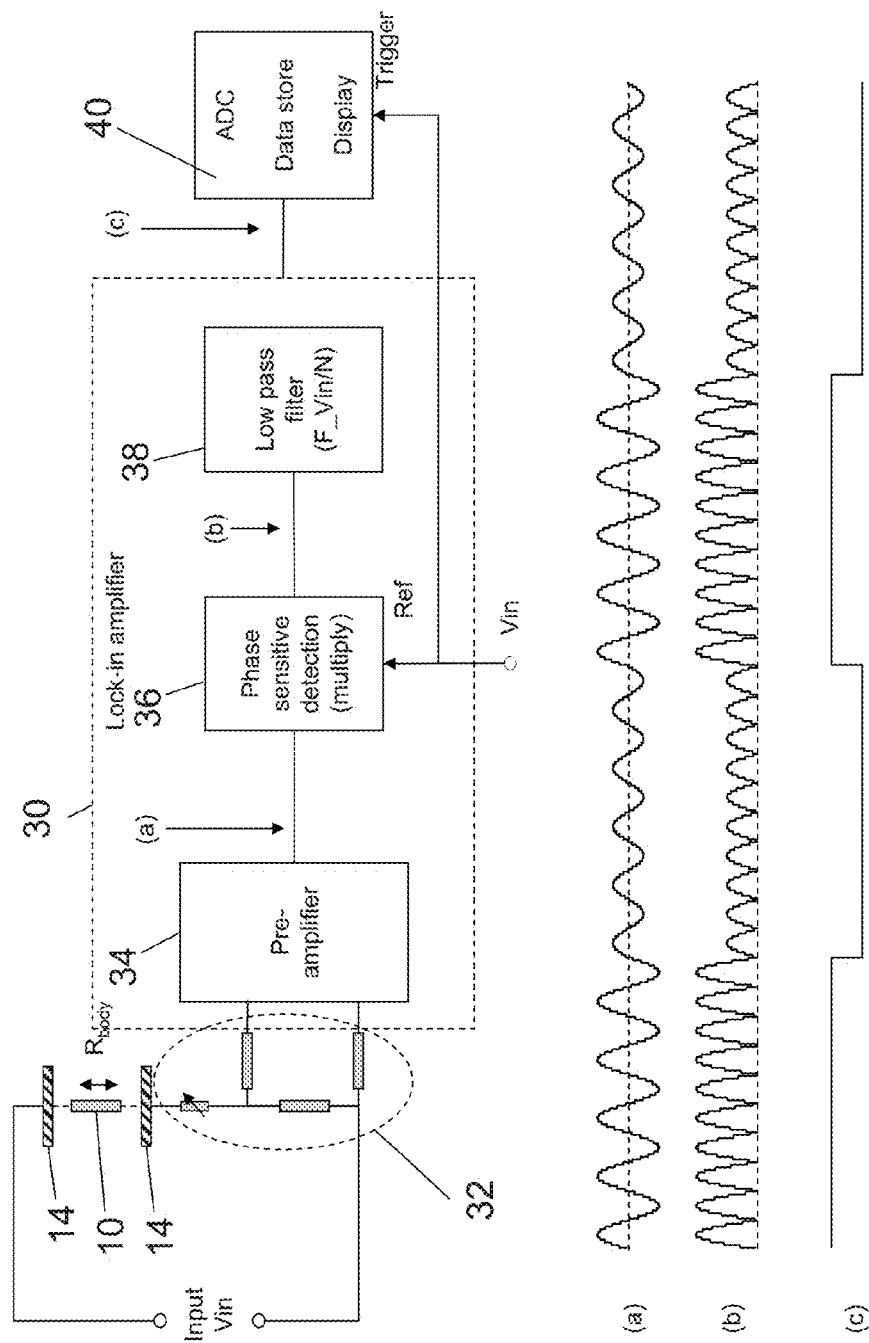
FIG. 4 shows a more detailed representation of an external device according to one or more embodiments of the invention.

According to one or more embodiments, in order to transmit data sensed by the implantable medical device 10 to an external device 12, a telemetry unit may be provided. In at least one embodiment, the telemetry unit may allow a bidirectional data communication, that is, the telemetry unit may transmit and receive data wirelessly. FIGS. 3 and 4 illustrate details of internal and external therapy units, respectively, according to one or more embodiments the invention.

Referring to FIG. 3, in at least one embodiment, the implantable medical device 10 may include two (implantable) electrodes 18 that may contact body tissue surrounding the implantable medical device 10 in its implanted state. In embodiments of the invention, at least one switch may be at least one simple switch 16 that may connect and/or disconnect, respectively, the two electrodes 18 in order to establish or interrupt an electrical connection between the electrodes. The electrical connection across the at least one switch 16 may be of low ohmic resistance, sufficiently low to detectably decrease the volume impedance of the tissue surrounding the implanted medical device. In at least one embodiment, the at least two electrodes 18 of the implantable medical device 10 may be arranged on the external surface of a hermetically sealed housing encapsulating the implantable medical device 10. According to one or more embodiments, parts of the housing itself may form the at least two electrodes 18.

In order to control the at least one switch 16, by way of one or more embodiments, the implantable medical device 10 may include a frequency divider 20 that may be connected to a sine-to-square converting comparator 22 that in turn may be connected to a phase-locked loop 24. Phase-locked loop 24, in embodiments of the invention, may be connected to the electrodes 18 via a band pass filter 26. Phase-locked loop 24 and frequency divider 20 may be part of a switch control of implantable medical device 10.

In at least one embodiment of the invention, the field induced between the cutaneous electrodes may be sensed by the implantable medical device 10. The implantable medical device 10 may lock in the frequency of the electric field using a phase-locked loop 24. Once the implantable medical device 10 is locked on to the frequency of the external device's induced field, in one or more embodiments, it may activate the at least one switch 16 between two electrodes 18 that may be in the field (as shown in FIGS. 2 and 3 for example) in synch with the frequency of the electric field.

In more detail, according to one or more embodiments, the implantable medical device 10 may sense the imposed oscillatory electric signal as input signal that may be detected via the electrodes 18 or across a resistor. Thus, in at least one embodiment, the implantable medical device may include an input sine signal that may be detected as an alternating voltage across electrodes 18 or across a resistor. This input sine signal may be band pass filtered by band pass filter 26. A representation of the band pass filtered signal is shown in diagram (a) of FIG. 3.

By way of one or more embodiments, the band pass filtered input sine signal may be fed to the phase-locked loop (PLL) 24 that may lock in the frequency of the input sine signal. Phase-locked loop 24, in at least one embodiment, may output a synchronized sine signal to a comparator 22 that may convert the sine signal to a square signal. The square signal generated, in embodiments of the invention, may be fed to frequency divider 20 that may generate a clock for switching the at least one switch 16. The clock generated, in one or more embodiments, may include a frequency corresponding to a fraction of the frequency of the oscillatory electric field wherein the fraction may be determined by a frequency division factor applied by frequency divider 20.

Alternatively, in at least one embodiment, a control device to control the at least one switch 16 of the implantable medical device 10 may be connected to a pulse modulator which may not be synchronized to the external electric field. For sufficiently low switching frequencies relative to the external field oscillatory frequency, for example 1:100 frequency ratio, in at least one embodiment, the impact of lack of external field phase synchrony to the impedance modulation caused by switching may be low. Only 1% sensitivity reduction of the external devices ability to detect the impedance changes induced by the implantable medical device would be caused by lack of phase synchrony for this example ratio.

The actual switching of the at least one switch 16 may further depend on data that may be transmitted from the implantable medical device 10 to the external device 12, according to embodiments of the invention. This data to be transmitted may be coded and the code may determine the actual sequence of switching of the at least one switch 16.

In one or more embodiments, frequency divider 20 may be a flip-flop counter. In embodiments of the invention, the at least one switch 16 may have a small on-resistance (preferably less than the volume impedance of tissue in which the device is implanted), which may lead to change of impedance of the tissue volume containing the implanted medical device, depending on whether the at least one switch 16 is opened or closed.

In at least one embodiment, such change of impedance may be sensed by external device 12.

In one or more embodiments, data transmission from the implantable medical device to the external device may be summarized as follows:

Apply signal (oscillatory electric field)→propagate in body→switch on/off of the at least one switch 16 in implantable device→impedance change of body→detect change by external device.

By way of one or more embodiments, during phase-synchronization, the switch control of the implantable medical device 10 may receive an input sine signal by detecting a voltage across electrodes 18 or across a resistor. The switch control of the implantable medical device 10 according to at least one embodiment of the invention, as shown in FIG. 3, may include a band pass filter 26, phase-locked loop 24 that may lock in the frequency of the input sine signal, comparator 22 that may convert the sine signal to a square signal, a flip-flop counter that may act as frequency divider 20 that control the at least one switch 16. In embodiments of the invention, the at least one switch 16 may include a small on-resistance.

In at least one embodiment, during free-running switch control, the switch control of the implantable medical device 10 may control the at least one switch 16 opening and closing without regard to the phase of the external electrical field. The at least one switch 16, in at least one embodiment, may have a small on-resistance relative to the tissue volume impedance in which it is implanted.

FIG. 4 shows a more detailed representation of an external device according to one or more embodiments of the invention. In at least one embodiment, the impedance changes caused by the implantable medical device 10 may be detected by the external device 12. As shown in FIG. 4, the external device 12 may include a lock-in amplifier that may generate an output signal (signal c) that may represent the signal transmitted by implantable medical device 10 by way of impedance changes. Lock-in amplifier 30, in one or more embodiments, may use the signal imposed on a body using cutaneous electrodes 14 as a reference signal. For this purpose, a network of resistors 32 may be provided that may cause a voltage drop representing the signal (the oscillatory electric field) imposed on a body via cutaneous electrodes 14.

In at least one embodiment, this signal may be amplified by pre-amplifier 34 of lock-in amplifier 30.

By way of one or more embodiments, the amplified signal sensed via cutaneous electrodes 14 and the resistor network 32 may be fed to an AM demodulator that may include a phase-sensitive detector 36 and further fed to a low pass filter 38, as depicted in FIG. 4. The amplified input signal sensed via cutaneous electrodes 14 and the resistor network 32 is represented as signal (a) in FIG. 4. The output signal of the phase-sensitive detector 36 is depicted in FIG. 4 as signal (b). The low pass filtered output signal of lock-in amplifier 30 is depicted in FIG. 4 as signal (c). Signal (c), in at least one embodiment, may correspond to the signal generated by implantable medical device 10 and thus may represent data to be transmitted from implantable medical device 10 to external device 12. In embodiments of the invention, this signal may be analog-to-digital converted and stored. Block 40 in FIG. 4 represents an analog-to-digital converter (ADC), a memory for data storage and a display of external device 12.

For the detection of impedance changes of body caused by the implantable medical device 10 the external device 12, in at least one embodiment, may include a lock-in amplifier that may use the input as reference signal, comprising an AM demodulator, which in turn may include a precision rectifier and a low-pass filter. In embodiments of the invention, the low pass filtered signal may be fed to an analog-to-digital converter or level discriminator in order to digitize the received signal. Due to the sensitivity of the phase locked demodulator (lock-in amplifier), the impedance changes detected may be very small, on the order of −120 dB.

The communication from implantable medical device 10 to external device 12 may be understood as follows.

As the implantable medical device 10 alternatively shorts and opens the connection between the electrodes 18, in one or more embodiments, the impedance between the external device electrodes 14 may be slightly changed or modulated. The external device 12 may sense the change in impedance by measuring how much voltage or current is imparted on the electrodes 14 to create the oscillator electric field between the external device electrodes 14.

In at least one embodiment, the external device 12 may sense the change in impedance using a lock-in amplifier that may be synchronized to the electric field frequency and phase. As the implantable medical device 10 modulates the impedance between the external device electrodes 14, in at least one embodiment, the external device 12 may integrate the changing current or voltage. The integration may allow a very small change in sourced voltage or current to be detected using amplitude modulation.

Figure 5:
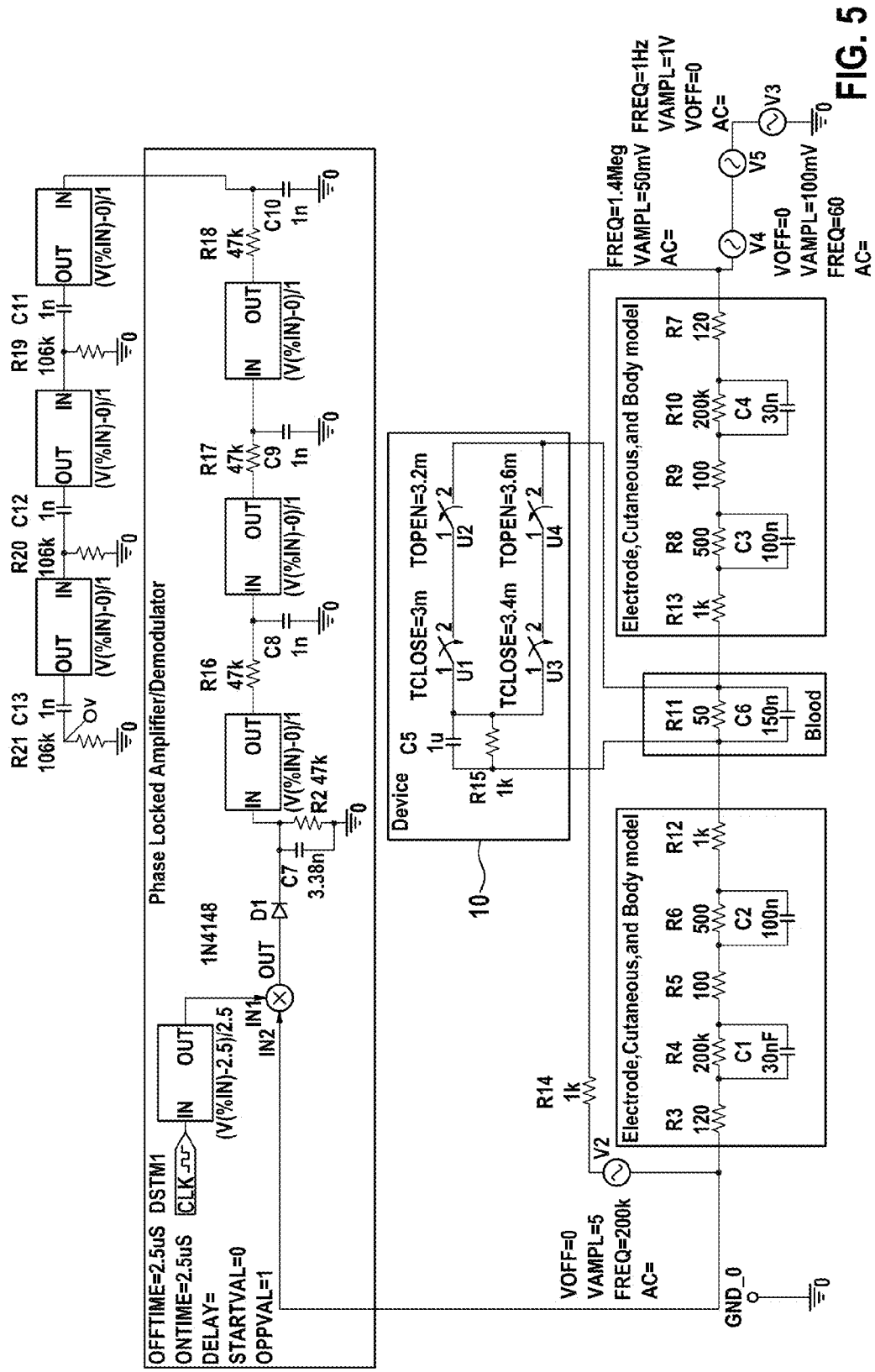
FIG. 5 shows a circuit diagram for a simulation scenario for simulating impedance change based data communication according to one or more embodiments of the invention.
Figure 6:
FIG. 6 shows a plot illustrating a simulation result achieved by using the diagram depicted in FIG. 5 according to one or more embodiments of the invention.

In one or more embodiments, communication may occur at approximately $\frac{1}{10}$ to $\frac{1}{1000}$th of the modulation frequency of the oscillatory electric field. This allows for ~10-1000 cycles of the electric field to be integrated to determine the imparted current or voltage. A model and simulation of the passive z-com embodiment is shown in FIGS. 5 and 6 as will be discussed below.

In at least one embodiment, a small electric field may be generated by the implanted device in place of passive resistance changes. In more detail, an external device 12 may generate a first oscillating electric field using cutaneous electrodes 14. In one or more embodiments, the implanted device 10 may detect the first oscillating electric field by electrodes 18 and may acquire a phase lock to the first oscillating electric field using a phase locked loop. The externally induced first oscillatory electric field may briefly be turned off by the external device, while the phase locked loop maintains its phase information. In embodiments of the invention, the implanted device may then generate a second oscillatory electric field using electrodes, the field having a fixed phase relationship with the first oscillatory electric field. The external device 12 may detect and demodulate the second oscillatory electric field by cutaneous electrode 14 and a phase-locked demodulator. Changing amplitude, phase, or other common modulation techniques, in embodiments of the invention, may be used by the implanted medical device to modulate the second oscillatory electric field, thus including a communications device to transmit data to the external device 12.

In at least one embodiment, the implanted device may switch its impedance or small electric field at every other crest of the external device's applied electric field for ~10-1000 cycles, called a chirp, in order to represent a mark of the communications scheme.

In one or more embodiments, a communication from external device 12 to implantable medical device 10 may be done as follows:

The imposed oscillatory electric field may include a fundamental frequency that the implantable medical device 10 uses to lock onto. The fundamental frequency may also be used as a carrier frequency to send modulated data to the implantable medical device 10. The external device 12 may modulate data, in at least one embodiment, using frequency modulation or amplitude modulation, on top of the carrier imparted electric field. In embodiments of the invention, the implantable medical device 10 may decode the modulated data sensed through the electrodes.

Embodiments of the invention may not require the implanted medical device 10 to actively transmit data using its own power in the case of impedance modulation embodiment. In embodiments of the invention, implanted medical device 10 may modulate a field imparted on it by an external device 12. In embodiments of the invention where the device may emit a low amplitude electric field, the phase-locked property that it maintains may allow for lower amplitude to be used for transmission to the external device 12 than if simple band-limited transmission schemes were used. In embodiments of the invention, the resulting drain on the medical device's battery may be extremely small. Because of the small power consumption, it may be possible to transmit more data to the external device 12.

FIGS. 5 and 6 illustrate a simulation of passive impedance-based data communication. Specifically, FIG. 5 shows a circuit diagram for a simulation scenario for simulating impedance change based data communication according to one or more embodiments of the invention, and FIG. 6 shows a plot illustrating a simulation result achieved by using the diagram depicted in FIG. 5 according to one or more embodiments of the invention.

Standard electrode-electrolyte-body impedance models and blood impedance models, according to one or more embodiments, may be combined with a lock-in demodulator in a model of the passive impedance implementation of the invention. Each simulation component is labeled, with the 'device' modeled in box labeled with "10" with access impedance and four closing switches to simulate the communication of two data bits to the external receiver/demodulator. In at least one embodiment, environmental and breathing noise may be induced in the model with voltage sources V3, V4, and V5 simulating line noise, RF noise, and breathing, body changing impedance noise, respectively.

The simulation signal at output filter resistor R21, in at least one embodiment, is shown as the green trace in FIG. 6. The impedance changes, in embodiments of the invention, may be at a detectable level (showing 2 bits) beyond the background noise that has been filtered out due to the lock-in receiver system. The slope to the left of this plot shows the final settling time of the filters.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method of communicating data from an implantable device to an external device, the method comprising:
    imposing an oscillatory electric field on body tissue surrounding an implantable device,
    sensing the oscillatory electric field imposed on the body tissue via the implantable device,
    one or more of
        altering the oscillatory electric field via the implantable device, by
            inducing an alternating change of impedance via the implantable device or
            generating a small oscillatory electric field via the implantable device, and
        generating a second oscillatory electric field which is phase synchronized to the oscillatory electric field imposed on the body tissue via the implantable device, and
    sensing the change of impedance or the small oscillatory electric field generated by the implantable device, respectively, using an external device, wherein the external device comprises or is connected to at least two cutaneous electrodes;
    wherein the altering of the oscillatory electric field via the implantable device is performed by at least two electrodes operatively connected to or part of the implantable device, and by at least one switch operatively connected to the at least two electrodes,
        wherein the at least one switch is configured to connect and disconnect the at least two electrodes in an alternating manner according to a code generated by the implantable device representing data to be transmitted from the implantable device to the external device, and
        wherein said alternating connecting and disconnecting of the at least two electrodes causes a detectable change of impedance of the imposed oscillatory electric field; and, wherein the at least one switch is connected to a switch control, and further comprising synchronizing the connecting and disconnecting of the at least two electrodes with the oscillatory electric field imposed on the body tissue via the switch control.

2. The method according to claim 1, wherein the sensing of the change of impedance comprises sensing a current or voltage over the at least two cutaneous electrodes and integrating a sensed voltage or current over a number of cycles of the oscillatory electric field, wherein said number of cycles correspond to a frequency division factor of a frequency divider of the implantable device.

3. The method according to claim 1, further comprising communicating data from the external device to the implantable device, and further comprising modulating the oscillatory electric field using the external device.

4. The method according to claim 3, wherein the oscillatory electric field imposed on the body comprises a fundamental frequency that the implantable device uses to lock onto.

5. The method according to claim 4, wherein the fundamental frequency is used as a carrier frequency to send modulated data from the external device to the implantable device.

6. The method according to claim 1, wherein the sensing of the change of impedance comprises sensing a current or voltage using the external device, and further comprising demodulating the change of impedance sensed to generate a communication scheme to transmit data from the implantable device to the external device.

7. The method according to claim 1, wherein the code comprises a clock, and wherein the clock is a fraction of a frequency of the oscillatory electric field imposed on the body tissue surrounding the implantable device.

8. The method according to claim 1, wherein said detectable change of impedance of the imposed oscillatory electric field is detected by the external device by measuring an amount of voltage or current imparted on the at least two cutaneous electrodes.

9. A method of communicating data from an implantable device to an external device, the method comprising:
   imposing an oscillatory electric field on body tissue surrounding an implantable device,
   sensing the oscillatory electric field imposed on the body tissue via the implantable device,
   one or more of
      altering the oscillatory electric field via the implantable device, by
         inducing an alternating change of impedance via the implantable device or
         generating a small oscillatory electric field via the implantable device, and
      generating a second oscillatory electric field which is phase synchronized to the oscillatory electric field imposed on the body tissue via the implantable device, and
   sensing the change of impedance or the small oscillatory electric field generated by the implantable device, respectively, using an external device, wherein the external device comprises or is connected to at least two cutaneous electrodes,
   wherein the sensing of the change of impedance comprises sensing a current or voltage over the at least two cutaneous electrodes and integrating a sensed voltage or current over a number of cycles of the oscillatory electric field, wherein said number of cycles correspond to a frequency division factor of a frequency divider of the implantable device.

10. A method of communicating data from an implantable device to an external device, the method comprising:
   imposing an oscillatory electric field on body tissue surrounding an implantable device,
   sensing the oscillatory electric field imposed on the body tissue via the implantable device,
   one or more of
      altering the oscillatory electric field via the implantable device, by
         inducing an alternating change of impedance via the implantable device or
         generating a small oscillatory electric field via the implantable device, and
      generating a second oscillatory electric field which is phase synchronized to the oscillatory electric field imposed on the body tissue via the implantable device, and
   sensing the change of impedance or the small oscillatory electric field generated by the implantable device, respectively, using an external device, wherein the external device comprises or is connected to at least two cutaneous electrodes,
   wherein the altering of the oscillatory electric field via the implantable device is performed by at least two electrodes operatively connected to or part of the implantable device, and by at least one switch operatively connected to the at least two electrodes,
   wherein the at least one switch is configured to connect and disconnect the at least two electrodes in an alternating manner according to a code generated by the implantable device representing data to be transmitted from the implantable device to the external device,
   wherein said alternating connecting and disconnecting of the at least two electrodes causes a detectable change of impedance of the imposed oscillatory electric field, and,
   wherein the code comprises a clock, and wherein the clock is a fraction of a frequency of the oscillatory electric field imposed on the body tissue surrounding the implantable device.

* * * * *